(12) United States Patent
Riley et al.

(10) Patent No.: US 9,835,624 B2
(45) Date of Patent: Dec. 5, 2017

(54) COMPOSITIONS AND METHODS FOR DETECTING MYCOBACTERIUM

(75) Inventors: Lee W. Riley, Berkeley, CA (US); Richard A. Mathies, Moraga, CA (US); Amador Goodridge, Berkeley, CA (US); Jungkyu Kim, Albany, CA (US); Robert Eugene Snyder, Berkeley, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 452 days.

(21) Appl. No.: 14/111,677

(22) PCT Filed: Apr. 16, 2012

(86) PCT No.: PCT/US2012/033741
§ 371 (c)(1),
(2), (4) Date: Jan. 27, 2014

(87) PCT Pub. No.: WO2012/151039
PCT Pub. Date: Nov. 8, 2012

(65) Prior Publication Data
US 2014/0162283 A1  Jun. 12, 2014

Related U.S. Application Data

(60) Provisional application No. 61/481,350, filed on May 2, 2011.

(51) Int. Cl.
| | | |
|---|---|---|
| *A61K 39/04* | (2006.01) |
| *A61K 39/395* | (2006.01) |
| *A61K 39/40* | (2006.01) |
| *G01N 33/569* | (2006.01) |
| *G01N 33/68* | (2006.01) |

(52) U.S. Cl.
CPC ..... *G01N 33/5695* (2013.01); *G01N 33/6854* (2013.01); *G01N 2469/20* (2013.01); *G01N 2800/52* (2013.01)

(58) Field of Classification Search
CPC ........ A61K 39/00; A61K 39/02; A61K 39/04; A61K 39/395; A61K 39/40
USPC ......... 424/130.1, 164.1, 168.1, 184.1, 234.1, 424/248.1
See application file for complete search history.

(56) References Cited

U.S. PATENT DOCUMENTS

| | | |
|---|---|---|
| 2002/0150588 A1 | 10/2002 | Allison et al. |
| 2007/0020691 A1 | 1/2007 | Kanter et al. |
| 2007/0110770 A1 | 5/2007 | van der Elzen et al. |
| 2008/0241128 A1 | 10/2008 | Jeffrey |

OTHER PUBLICATIONS

Santiago, M.B., et al. Anticardiolipin antibodies in patients with Infectious diseases. Clinical rheumatology, vol. 8, No. 1, pp. 23-28, 1989.*
Goodridge et al., "Anti-Phospholipid Antibody Levels as Biomarker for Monitoring Tuberculosis Treatment Response", 2012, Tuberculosis, 92(3):243-247.
Kalra, et al., "Correlation of Antibody IgM With First Trimester Recurrent Abortions", J. Anat. Soc. India, 2002, 51(1):10-13.

* cited by examiner

*Primary Examiner* — Rodney P Swartz
(74) *Attorney, Agent, or Firm* — Bozicevic Field & Francis, LLP; Paula A. Borden

(57) ABSTRACT

The present disclosure provides methods of detecting *mycobacterium* in an individual, generally involving detecting antibody to a mycobacterial lipid in a biological sample obtained from the individual. The present disclosure further provides compositions and kits for carrying out the methods.

22 Claims, 3 Drawing Sheets

COMPOSITIONS AND METHODS FOR DETECTING MYCOBACTERIUM

CROSS-REFERENCE

This application claims the benefit of U.S. Provisional Patent Application No. 61/481,350, filed May 2, 2011, which application is incorporated herein by reference in its entirety.

STATEMENT REGARDING FEDERALLY SPONSORED RESEARCH

This invention was made with government support under Grant No. 1R01AI073204 awarded by National Institutes of Health. The government has certain rights in the invention.

BACKGROUND

Tuberculosis (TB) is an infectious disease that kills more adults than any other infectious disease worldwide. Every year, 8.9-9.9 million new cases of TB are estimated by the World Health Organization to occur globally. The disease is caused by bacterium *Mycobacterium tuberculosis*, which can reside in an infected host for many years. Most infected people remain latently infected with the organism, but a subset of infected individuals will reactivate the infection and develop active disease. Timely treatment of those who develop active disease is critical for preventing further transmissions to others. Treatment requires reliable, rapid diagnosis of the disease.

The problem is that in most countries endemic for TB, the diagnosis of the disease is hampered by the lack of resources to culture the organism, which is especially needed to diagnose drug-resistant forms of the disease. As such, in most countries, including in the United States, the treatment of the disease is often initiated empirically, without the knowledge of the drug-susceptibility of the causative agent. In someone who has drug-resistant TB, such a method of treatment often fails.

There is a need in the art for methods of determining whether an individual who is being treated for TB is responding to such treatment.

SUMMARY

The present disclosure provides methods of detecting the level of a *mycobacterium* in an individual, generally involving detecting antibody to a mycobacterial lipid in a biological sample obtained from the individual. The present disclosure further provides compositions and kits for carrying out the methods.

DEFINITIONS

Figure 1:
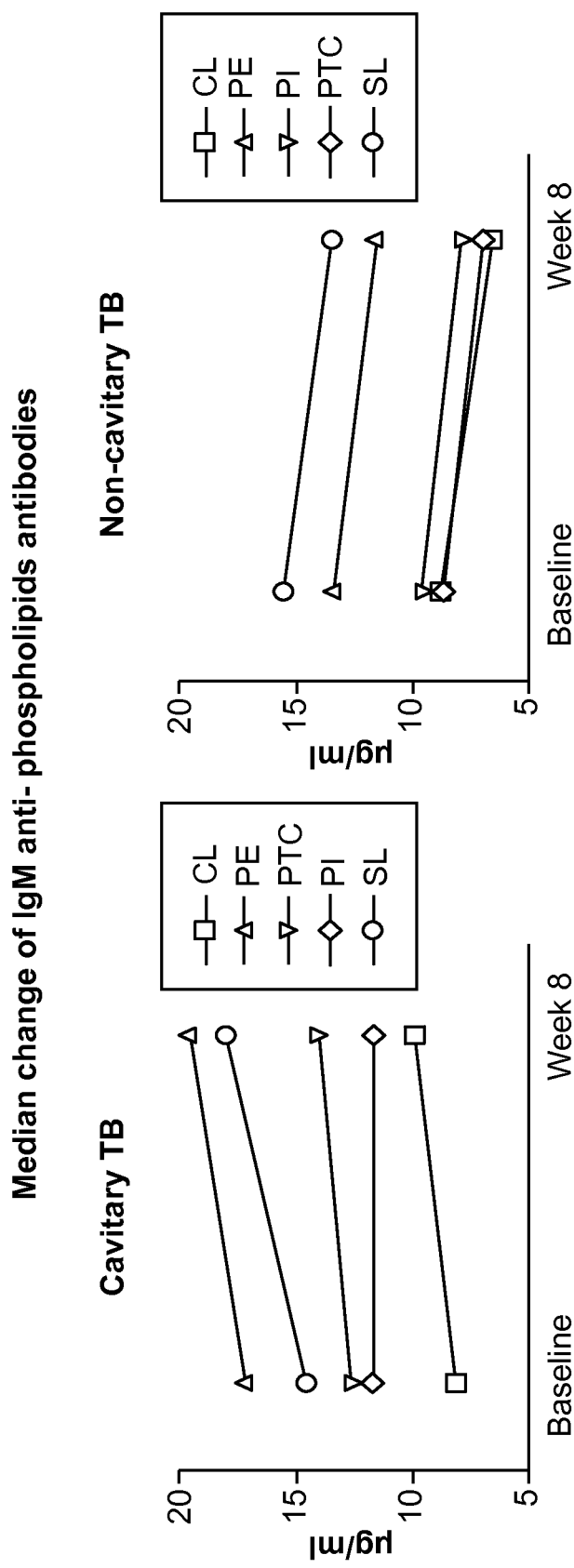
FIG. 1 depicts plots of the change of IgM anti-phospholipids antibody levels after 40 doses of intense anti-TB drug therapy (CL-cardiolipin, PI-phosphatidylinositol, PE-phosphatidylethanolamine, PTC-phosphatidylcholine, and SL-sphingolipid).

A "biological sample" encompasses a variety of sample types obtained from an individual and can be used in a subject assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components. The term "biological sample" encompasses a clinical sample, and also includes cells in culture, cell supernatants, cell lysates, serum, plasma, biological fluid, and tissue samples. A "biological sample" can include biological fluids such as blood; a blood fraction such as serum or plasma; cerebrospinal fluid; pleural fluid; bronchoalveolar lavage fluid; and saliva. A "biological sample" can include a biological fluid that has been manipulated in any way.

The terms "antibodies" and "immunoglobulin" include antibodies or immunoglobulins of any isotype, fragments of antibodies which retain specific binding to antigen, including, but not limited to, Fab, Fv, scFv, and Fd fragments, chimeric antibodies, humanized antibodies, single-chain antibodies, and fusion proteins comprising an antigen-binding portion of an antibody and a non-antibody protein. The antibodies may be detectably labeled, e.g., with a radioisotope, an enzyme which generates a detectable product, a fluorescent protein, and the like. The antibodies may be further conjugated to other moieties, such as members of specific binding pairs, e.g., biotin (member of biotin-avidin specific binding pair), and the like. The antibodies may also be bound to a solid support, including, but not limited to, polystyrene plates or beads, and the like. Also encompassed by the term are Fab', Fv, F(ab')$_2$, and or other antibody fragments that retain specific binding to antigen, and monoclonal antibodies. An antibody may be monovalent or bivalent.

"Antibody fragments" comprise a portion of an intact antibody, for example, the antigen binding or variable region of the intact antibody. Examples of antibody fragments include Fab, Fab', F(ab')$_2$, and Fv fragments; diabodies; linear antibodies (Zapata et al., Protein Eng. 8(10): 1057-1062 (1995)); single-chain antibody molecules; and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')$_2$ fragment that has two antigen combining sites and is still capable of cross-linking antigen.

"Axial flow" as used herein refers to lateral, vertical or transverse flow through a particular matrix or material comprising one or more test and/or control zones. The type of flow contemplated in a particular device, assay or method varies according to the structure of the device. Without being bound by theory, lateral, vertical or transverse flow may refer to flow of a fluid sample from the point of fluid contact on one end or side of a particular matrix (the upstream or proximal end) to an area downstream (or distal) of this contact. The downstream area may be on the same side or on the opposite side of the matrix from the point of fluid contact. For example, in vertical flow devices of the present invention, axial flow may progress vertically from and through a first member (top to bottom) to a second member and from there on to an absorbent medium. By way of further example, and as will be appreciated by those of skill in the art, in a vertical flow device configured, for example, as a dipstick, a fluid sample may flow literally up the device, in which case however, the point of first contact of the fluid sample to the device is nonetheless considered the upstream (i.e., proximal) end and the point of termination of flow the downstream (i.e., distal) end.

As used herein the terms "upstream" and "downstream" refer to the direction of fluid sample flow subsequent to contact of the fluid sample with a representative device of the present disclosure, wherein, under normal operating conditions, the fluid sample flow direction runs from an upstream position to a downstream position. For example, when fluid sample is initially contacted with the sample receiving zone, the fluid sample then flows downstream through the label zone and so forth.

The term "binding" refers to a direct association between two molecules, due to, for example, covalent, electrostatic, hydrophobic, and ionic and/or hydrogen-bond interactions, including interactions such as salt bridges and water bridges. An antibody specific for human IgM binds specifically to an epitope within a human IgM polypeptide (e.g., an epitope within the constant region of a human IgM polypeptide), e.g., with an affinity of at least about $10^{-7}$ M, at least about $10^{-8}$ M, at least about $10^{-9}$ M, at least about $10^{-10}$ M, at least about $10^{-11}$ M, or at least about $10^{-12}$ M, or greater than $10^{-12}$ M. An antibody specific for human IgM binds to an epitope present on a human IgM polypeptide with an affinity of from about $10^{-7}$ M to about $10^{-8}$ M, from about $10^{-8}$ M to about $10^{-9}$ M, from about $10^{-9}$ M to about $10^{-10}$ M, from about $10^{-10}$ M to about $10^{-11}$ M, or from about $10^{-11}$ M to about $10^{-12}$ M, or greater than $10^{-12}$ M. Non-specific binding would refer to binding with an affinity of less than about $10^{-7}$ M, e.g., binding with an affinity of $10^{-6}$ M, $10^{-5}$ M, $10^{-4}$ M, etc.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a lipid" includes a plurality of such lipids and reference to "the test device" includes reference to one or more test devices and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed, to the extent that such combinations embrace subject matter that are, for example, compounds that are stable compounds (i.e., compounds that can be made, isolated, characterized, and tested for biological activity). In addition, all sub-combinations of the various embodiments and elements thereof (e.g., elements of the chemical groups listed in the embodiments describing such variables) are also specifically embraced by the present invention and are disclosed herein just as if each and every such sub-combination was individually and explicitly disclosed herein.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION

The present disclosure provides methods of detecting the level of a *mycobacterium* in an individual, generally involving detecting antibody to a mycobacterial lipid in a biological sample obtained from the individual. The present disclosure further provides compositions and kits for carrying out the methods.

It was observed that antibody response to *Mycobacterium tuberculosis* lipids is a direct reflection of bacterial burden in a host infected with *M. tuberculosis*. That is, higher the number of *M. tuberculosis* bacteria in a host, the higher the antibody level the host mounts to lipids produced by the bacteria. A large proportion of the cell wall of *M. tuberculosis* is comprised of lipids. Thus, if treatment is successful, the antibody response to the lipids decreases. This approach makes it possible to apply a simple serologic test platform to determine the *M. tuberculosis* burden in an infected individual, and to determine an individual's response to treatment for an *M. tuberculosis* infection.

Methods of Determining the Level of *M. tuberculosis* in an Individual

The present disclosure provides methods of detecting the level of a *mycobacterium* (e.g., *M. tuberculosis*) in an individual. The methods generally involve determining the level of IgM specific for an *M. tuberculosis* lipid in a biological sample obtained from the individual. The level of *M. tuberculosis* lipid-specific IgM is directly correlated with the level of *M. tuberculosis* in the individual.

Lipids

An *M. tuberculosis* lipid is a lipid that can be synthesized by *M. tuberculosis*. Lipids produced by *M. tuberculosis* include, but are not limited to, cardiolipin, phosphatidylinositol, phosphatidylethanolamine, phosphatidylcholine, and sphingolipid.

Anti-IgM Antibody

Anti-IgM antibody suitable for use in a subject method includes antibody specific for human IgM, e.g., antibody specific for a constant region epitope of human IgM. In some cases, the anti-IgM antibody is a polyclonal antibody. In other cases, the anti-IgM antibody is a monoclonal antibody, or an antigen-binding fragment thereof.

An anti-IgM antibody will in some embodiments comprise a detectable label. Suitable detectable labels include any composition detectable by spectroscopic, photochemical, biochemical, immunochemical, electrical, optical or chemical means. Suitable include, but are not limited to, magnetic beads (e.g. Dynabeads™); fluorescent dyes (e.g., fluorescein isothiocyanate, texas red, rhodamine, and the like); a fluorescent protein, e.g., a green fluorescent protein, a red fluorescent protein, a yellow fluorescent protein, and the like; a chromogenic polypeptide; a radiolabel (e.g., $^3$H, $^{125}$I, $^{35}$S, $^{14}$C, or $^{32}$P); an enzyme that produces a colored product, a fluorescent product, or a luminescent product, (e.g., horse radish peroxidase, alkaline phosphatase, luciferase, and others commonly used in an enzyme-linked immunosorbent assay (ELISA)); and colorimetric labels such as colloidal gold or colored glass or plastic (e.g. polystyrene, polypropylene, latex, etc.) beads. In some cases, an anti-IgM antibody will comprise covalently linked colloidal gold.

In some cases, an anti-IgM antibody will be linked to a magnetic bead. As one non-limiting example, an anti-IgM antibody can be covalently linked to biotin; a magnetic bead can be coated with streptavidin; and the anti-IgM-biotin can bind to the streptavidin-magnetic bead, to form a stable anti-IgM-magnetic bead complex. Other means of linking an anti-IgM antibody to a magnetic bead are known in the art; and any such means can be used. For example, Protein G can be bound to (e.g., cross-linked to) a magnetic bead, and an anti-IgM antibody capable of binding to Protein G can be complexed with the Protein-G-magnetic bead. As another example, Protein A can be bound to (e.g., cross-linked to) a magnetic bead, and an anti-IgM antibody capable of binding to Protein A can be complexed with the Protein-A-magnetic bead.

Assay Formats

A subject method can be carried out using any of a variety of assay formats. For example, in some instances, lipids are attached to an insoluble support. Suitable insoluble supports can comprise various materials including, but not limited to, polyvinyl difluoride (PVDF), cellulose, nitrocellulose, nylon, glass, polystyrene, polyvinyl chloride, polypropylene, polyester terephthalate, polyethylene, polycarbonate, dextran, amylose, natural and modified celluloses, polyacrylamides, silica embedded in a polyacrylamide gel, agaroses, and magnetite and the like.

The insoluble support can be in any of a variety of formats (e.g., dimensions, shapes), e.g., sheets, such as used in a test strip or dipstick assay format.

Methods for attaching a lipid to an insoluble support include, e.g., direct attachment of the lipid to an insoluble support; modification of a lipid with a linker moiety, which linker moiety (e.g., a peptide) serves as the attachment point to the insoluble support; etc. A lipid (modified to include a linker moiety; or unmodified) can be covalently or non-covalently linked to an insoluble support.

In some cases, the assay format is a magnetic bead-linked immunosorbent assay (mLISA). As an example, a mycobacterial lipid (e.g., cardiolipin; phosphatidylethanolamine; phosphatidylinositol; phosphatidylcholine; sphingolipid; etc.) is applied to a solid support, and any unbound lipid is washed away, leaving immobilized lipid. A biological sample from an individual is applied to the lipid-bound solid support; any IgM specific for a mycobacterial lipid that is present in the biological sample will bind to the lipid, forming an immobilized IgM-lipid complex. Anti-IgM antibody bound to a magnetic bead (anti-IgM-magnetic bead) is then contacted with the immobilized IgM-lipid complex. Binding of the anti-IgM-magnetic bead to the immobilized IgM-lipid complex can be detected, e.g., by visual inspection or any other suitable method.

Subjects

An individual who is to be tested using a subject method includes individuals who have been diagnosed as having a mycobacterial infection, e.g., an infection with a *mycobacterium* that is a pathogen. Individuals include humans and non-human mammals (e.g., ungulates (e.g., bovines, ovines, porcines, etc.), canines, felines, etc.). In many instances, the individual is a human.

In some instances, the individual is a human who has, or is suspected of having, a mycobacterial infection, e.g., an infection with *Mycobacterium tuberculosis, M. bovis, M. africanum, M. canetti, M. microti, M. leprae, M. marinum, M. avium,* or *M. kansasii.* Individuals who have, or who are suspected of having, a mycobacterial infection can also include smokers (e.g., cigarette (tobacco) smokers), non-smokers, alcoholics, non-alcoholics, illegal drug users, non drug users, individuals infected with human immunodeficiency virus (HIV), individuals not infected with HIV, individuals with a healthy immune system, and immuno-compromised individuals. In some instances, the individual is apparently healthy; in other instance, the individual exhibits one or more symptoms of a mycobacterial infection.

In some instances, the individual is a human infected with *Mycobacterium tuberculosis.* The individual can be a human who has an *M. tuberculosis* infection, and who has been treated with a first-line drug for treating an *M. tuberculosis* infection. The individual can be a human who has an *M. tuberculosis* infection, and who has been treated with a second-line drug for treating an *M. tuberculosis* infection. The individual can be a human who has an *M. tuberculosis* infection, and who has been treated with a third-line drug for treating an *M. tuberculosis* infection.

First-line drugs for treating an *M. tuberculosis* infection include ethambutol, isoniazid, pyrazinamide, rifampicin, and streptomycin. An example of a treatment regimen including first-line drugs is isoniazid, rifampicin, ethambutol, and pyrazinamide daily for two months; followed by four months of isoniazid and rifampicin three times per week. Second-line drugs for treating an *M. tuberculosis* infection include aminoglycosides (e.g., amikacin; kanamycin); polypeptides such as capreomycin, viomycin, and enviomycin; fluoroquinolines such as ciprofloxacin, levofloxacin, moxifloxacin; thioamides such as ethionamide and prothionamide; cycloserine; and p-aminosalicylic acid. Third-line drugs for treating an *M. tuberculosis* infection include rifabutin; macrolides such as clarithromycin; linezolid; thioacetazone; thioridazine; arginine; vitamin D; and R207910.

In some instances, the individual is one who has been treated for an *M. tuberculosis* infection with a first-line drug or combination of first-line drugs; and who has become resistant to the first-line drug or the combination of first-line drugs, e.g., *M. tuberculosis* resistant to the first-line drug emerges in the individual. In some instances, the individual is infected with drug-resistant *M. tuberculosis*. For example, in some instances, the individual is infected with isoniazid-resistant *M. tuberculosis*. In some instances, the individual is infected with a multi-drug resistant strain of *M. tuberculosis*.

Individuals also include individuals who have an *M. tuberculosis* infection or an infection with a *mycobacterium* other than *M. tuberculosis*, and who have one or more other disorders. For example, individuals who may be tested with a subject method include individuals who have an *M. tuberculosis* infection; and who are infected with a human immunodeficiency virus (HIV), e.g., HIV-1. Individuals who may be tested with a subject method include individuals who have silicosis; and who have an *M. tuberculosis* infection. Individuals who may be tested with a subject method include individuals who are immunocompromised; and who have an *M. tuberculosis* infection.

Individuals who are suitable for testing using a subject method also include: 1) individuals with confirmed tuberculosis (verified TB cases), who have non-cavitary lung disease as evidenced by, e.g., chest x-ray; 2) individuals with confirmed tuberculosis with cavitary lung disease as evidenced by, e.g., chest x-ray; 3) individuals with extra-pulmonary tuberculosis; 4) individuals who are close contacts of an individual with confirmed tuberculosis (e.g., individuals who come into physical proximity with an individual with confirmed tuberculosis), where such close-contact individuals include, e.g., household contacts, schoolmates, co-workers, and friends; 5) individuals who are shown to have latent tuberculosis infection (*M. tuberculosis* infection) based on positive tuberculin skin test and/or gamma interferon release assays; 6) individuals with latent *M. tuberculosis* infection, who are undergoing preventive treatment for the infection; 7) Bacille Calmette-Guérin (BCG)-vaccinated individuals; 8) individuals with mono-resistant TB (e.g., individuals infected with *M. tuberculosis* that is resistant to a single drug used to treat *M. tuberculosis* infection); 9) individuals with multidrug-resistant TB (e.g., individuals infected with *M. tuberculosis* that is resistant to two or more drugs used to treat *M. tuberculosis* infection); and 10) individuals with extensively drug resistant (XDR) TB (e.g., individuals infected with XDR *M. tuberculosis*).

Individuals suitable for testing using a subject method include: 1) individuals with mono-resistant TB (e.g., individuals infected with *M. tuberculosis* that is resistant to a single drug used to treat *M. tuberculosis* infection), which individuals are undergoing treatment for the *M. tuberculosis* infection; 2) individuals with multidrug-resistant TB (e.g., individuals infected with *M. tuberculosis* that is resistant to two or more drugs used to treat *M. tuberculosis* infection), which individuals are undergoing treatment for the *M. tuberculosis* infection; and 3) individuals with XDR TB (e.g., individuals infected with XDR *M. tuberculosis*), which individuals are undergoing treatment for the *M. tuberculosis* infection. Treatments include those described above.

Generating a Report

A subject method can include generating a report that provides an indication of the level of mycobacteria in an individual. For example, the methods disclosed herein can further include a step of generating or outputting a report providing the results of a subject detection method, which report can be provided in the form of an electronic medium (e.g., an electronic display on a computer monitor), or in the form of a tangible medium (e.g., a report printed on paper or other tangible medium).

A subject report can further include one or more of: 1) service provider information; 2) patient data; 3) data regarding the level of mycobacteria; 4) follow-up evaluation recommendations; 5) therapeutic intervention recommendations; and 6) other features. A subject report can include, in addition to information regarding the level of mycobacteria (as determined by the level of mycobacterial lipid-specific IgM), patient information such as age, gender, body mass index (BMI), bilateral abnormalities, acid-fast bacillus (AFB) smear status, cavitary disease, and disease severity.

Based on the determined level of mycobacteria, and/or based on a report (as described above), a physician or other qualified medical personnel can determine whether appropriate modification in therapeutic regimen is advised.

Utility

A subject detection method finds use in various applications. For example, the present disclosure provides methods of determining the response of an individual to treatment for an *M. tuberculosis* infection. As another example, the present disclosure provides methods of detecting the presence of *M. tuberculosis* in an individual; e.g., methods of determining whether an individual has an *M. tuberculosis* infection.

Methods of Determining Response to Drug Treatment

The present disclosure provides methods of determining the response of an individual to treatment for an *M. tuberculosis* infection. The methods generally involve determining the level of IgM specific for an *M. tuberculosis* lipid in a biological sample obtained from the individual. A biological sample is obtained from an individual undergoing treatment for a mycobacterial infection; and the biological sample is tested to determine the level of IgM specific for an *M. tuberculosis* lipid.

A level of *M. tuberculosis* lipid-specific IgM in the biological sample that is lower than a pre-treatment level indicates that the individual is responding positively to the treatment. For example, a level of *M. tuberculosis* lipid-specific IgM in the biological sample that is at least about 10%, at least about 15%, at least about 20%, at least about 25%, at least about 30%, at least about 35%, at least about 40%, or at least about 50%, or more than 50%, lower than a pre-treatment level indicates that the individual is responding positively to the treatment.

Alternatively, a level of *M. tuberculosis* lipid-specific IgM in a biological sample obtained at a first time point during treatment for the *M. tuberculosis* infection is compared with the level of *M. tuberculosis* lipid-specific IgM in a biological sample obtained at a second time point during treatment for the *M. tuberculosis* infection, where the second time point is later than the first time point. Where the level of *M. tuberculosis* lipid-specific IgM is lower at the second time point than at the first time point indicates that the individual is responding positively to the treatment. For example, a level of *M. tuberculosis* lipid-specific IgM in a biological sample obtained at a second time point that is at least about 10%, at least about 15%, at least about 20%, at least about 25%, at least about 30%, at least about 35%, at least about 40%, or at least about 50%, or more than 50%, lower than the level of *M. tuberculosis* lipid-specific IgM in a biological sample obtained at a first time point indicates that the individual is responding positively to the treatment. The time period between the first time point and the second (later) time point can be from about 1 day to about 1 year (or more than 1 year), e.g., from about 1 day to about 7 days, from about 1 week to about 2 weeks, from about 2 weeks to about 4 weeks, from about 1 month to about 2 months, from about 2 months to about 6 months, or from about 6 months to about 1 year, or more than 1 year.

Subjects

An individual who is to be tested using a subject method includes an individual who has a mycobacterial infection (e.g., an infection with *Mycobacterium tuberculosis, M. bovis, M. africanum, M. canetti, M. microti, M. leprae, M. marinum, M. avium*, or *M. kansasii*) (e.g., an individual who has tested positive for a mycobacterial infection, e.g., using a PPD skin test); and who is undergoing treatment for the infection.

In some instances, the individual is a human infected with *Mycobacterium tuberculosis*. The individual can be a human who has an *M. tuberculosis* infection, and who has been treated with a first-line drug for treating an *M. tuberculosis* infection. The individual can be a human who has an *M. tuberculosis* infection, and who has been treated with a second-line drug for treating an *M. tuberculosis* infection. The individual can be a human who has an *M. tuberculosis* infection, and who has been treated with a third-line drug for treating an *M. tuberculosis* infection.

First-line drugs for treating an *M. tuberculosis* infection include ethambutol, isoniazid, pyrazinamide, rifampicin, and streptomycin. An example of a treatment regimen including first-line drugs is isoniazid, rifampicin, ethambutol, and pyrazinamide daily for two months; followed by four months of isoniazid and rifampicin three times per week. Second-line drugs for treating an *M. tuberculosis* infection include aminoglycosides (e.g., amikacin; kanamycin); polypeptides such as capreomycin, viomycin, and enviomycin; fluoroquinolines such as ciprofloxacin, levofloxacin, moxifloxacin; thioamides such as ethionamide and prothionamide; cycloserine; and p-aminosalicylic acid. Third-line drugs for treating an *M. tuberculosis* infection include rifabutin; macrolides such as clarithromycin; linezolid; thioacetazone; thioridazine; arginine; vitamin D; and R207910.

In some instances, the individual is one who has been treated for an *M. tuberculosis* infection with a first-line drug or combination of first-line drugs; and who has become resistant to the first-line drug or the combination of first-line drugs, e.g., *M. tuberculosis* resistant to the first-line drug emerges in the individual. In some instances, the individual is infected with drug-resistant *M. tuberculosis*. For example, in some instances, the individual is infected with isoniazid-resistant *M. tuberculosis*. In some instances, the individual is infected with a multi-drug resistant strain of *M. tuberculosis*.

Individuals also include individuals who have an *M. tuberculosis* infection or an infection with a *mycobacterium* other than *M. tuberculosis*, and who have one or more other disorders. For example, individuals who may be tested with a subject method include individuals who have an *M. tuberculosis* infection; and who are infected with a human immunodeficiency virus (HIV), e.g., HIV-1. Individuals who may be tested with a subject method include individuals who have silicosis; and who have an *M. tuberculosis* infection. Individuals who may be tested with a subject method include individuals who are immunocompromised; and who have an *M. tuberculosis* infection.

Generating a Report

A subject method can include generating a report that provides an indication of an individual's response to drug treatment for a mycobacterial infection. For example, the methods disclosed herein can further include a step of generating or outputting a report providing the results of a subject diagnostic method, which report can be provided in the form of an electronic medium (e.g., an electronic display on a computer monitor), or in the form of a tangible medium (e.g., a report printed on paper or other tangible medium).

A subject report can further include one or more of: 1) service provider information; 2) patient data; 3) data regarding the response to drug treatment for a mycobacterial infection; 4) follow-up evaluation recommendations; 5) therapeutic intervention recommendations; and 6) other features. A subject report can include, in addition to information regarding the level of mycobacteria (as determined by the level of mycobacterial lipid-specific IgM), patient information such as age, gender, body mass index (BMI), bilateral abnormalities, acid-fast bacillus (AFB) smear status, cavitary disease, and disease severity.

Based on the assessment of the individual's response to drug treatment for a mycobacterial infection, and/or based on a report (as described above), a physician or other qualified medical personnel can determine whether appropriate modification in therapeutic regimen is advised.

Diagnostic Methods

The present disclosure provides methods of detecting the presence of *M. tuberculosis* in an individual. The presence of *M. tuberculosis* in an individual can indicate that the individual has an *M. tuberculosis* infection. Thus, the present disclosure provides methods of determining whether an individual has an *M. tuberculosis* infection. The methods generally involve determining the level of IgM specific for an *M. tuberculosis* lipid in a biological sample obtained from the individual.

Thus, the present disclosure provides a method for detecting the presence of *Mycobacterium tuberculosis* in an individual, the method comprising detecting IgM specific for a *Mycobacterium tuberculosis* lipid in a liquid biological sample obtained from the individual. The presence in the biological sample of IgM specific for a *Mycobacterium tuberculosis* lipid indicates the presence in the individual of *Mycobacterium tuberculosis*.

A level of *M. tuberculosis* lipid-specific IgM in the biological sample that is higher than a normal, control level indicates the presence of *M. tuberculosis* in the individual, and can indicate that the individual has an *M. tuberculosis* infection. For example, a level of *M. tuberculosis* lipid-specific IgM in the biological sample that is at least about 20%, at least about 25%, at least about 30%, at least about 35%, at least about 40%, at least about 50%, at least about 2-fold, at least about 5-fold, or more than 5-fold, higher than a normal, control level indicates the presence of *M. tuberculosis* in the individual, and can indicate that the individual has an *M. tuberculosis* infection.

A normal, control level of *M. tuberculosis* lipid-specific IgM is a level, or a range of levels, that is found in individuals who have tested negative for *M. tuberculosis* infection, using, e.g., a tuberculosis skin test (also known as the "purified protein derivative" or "PPD" tuberculin skin test).

Subjects

Subjects who can undergo a subject diagnostic method to determine the presence of *M. tuberculosis* include individuals who have never previously been tested for *M. tuberculosis* infection; individuals who have been previously tested (e.g., using the PPD tuberculin skin test) for *M. tuberculosis* infection; individuals who are at greater risk than the general population of having an *M. tuberculosis* infection. Individuals who are at greater risk than the general population of having an *M. tuberculosis* infection include, e.g., HIV-1-infected individuals; long-term alcohol or drug abusers; immunocompromised individuals; individuals who frequently travel to or who have travelled to countries in which the rate of tuberculosis is high; individuals living in crowded facilities (e.g., prisons); and the like.

Treatment

In some cases, an individual who is diagnosed as having an *M. tuberculosis* infection, using a subject detection method, is then treated for the *M. tuberculosis* infection. For example, the individual can be treated with a first-line drug for treating an *M. tuberculosis* infection.

First-line drugs for treating an *M. tuberculosis* infection include ethambutol, isoniazid, pyrazinamide, rifampicin, and streptomycin. An example of a treatment regimen including first-line drugs is isoniazid, rifampicin, ethambutol, and pyrazinamide daily for two months; followed by four months of isoniazid and rifampicin three times per week. Second-line drugs for treating an *M. tuberculosis* infection include aminoglycosides (e.g., amikacin; kanamycin); polypeptides such as capreomycin, viomycin, and enviomycin; fluoroquinolines such as ciprofloxacin, levofloxacin, moxifloxacin; thioamides such as ethionamide and prothionamide; cycloserine; and p-aminosalicylic acid. Third-line drugs for treating an *M. tuberculosis* infection include rifabutin; macrolides such as clarithromycin; linezolid; thioacetazone; thioridazine; arginine; vitamin D; and R207910.

Generating a Report

A subject method can include generating a report that indicates whether an individual has a mycobacterial infection (e.g., an *M. tuberculosis* infection). For example, the methods disclosed herein can further include a step of generating or outputting a report providing the results of a subject diagnostic method, which report can be provided in the form of an electronic medium (e.g., an electronic display on a computer monitor), or in the form of a tangible medium (e.g., a report printed on paper or other tangible medium).

A subject report can further include one or more of: 1) service provider information; 2) patient data; 3) presence or absence of a mycobacterial infection; 4) follow-up evaluation recommendations; 5) therapeutic intervention recommendations; and 6) other features. A subject report can include, in addition to information regarding the level of mycobacteria (as determined by the level of mycobacterial lipid-specific IgM), patient information such as age, gender, body mass index (BMI), bilateral abnormalities, acid-fast bacillus (AFB) smear status, cavitary disease, and disease severity.

Based on an assessment of the presence in the individual of a mycobacterial infection, and/or based on a report (as described above), a physician or other qualified medical personnel can determine an appropriate therapeutic regimen.

Kits and Assay Devices

The present disclosure provides a kit for carrying out a method of the present disclosure, e.g., a method of detecting, in a biological sample obtained from an individual, the level of IgM specific for a mycobacterial lipid. The present disclosure further provides an assay device for carrying out a method of the present disclosure, e.g., a method of detecting, in a biological sample obtained from an individual, the level of IgM specific for a mycobacterial lipid.

Kits

A subject kit can include: a) a binding reagent (e.g., an antibody) that specifically binds human IgM; b) one or more mycobacterial lipids; and c) a control (e.g., a positive control; a negative control). A subject kit can also include purified human IgM for use in generating a standard curve, e.g., where the purified human IgM is provided in known amount that can be diluted to generate a standard curve. A subject kit can include a panel of positive control IgM antibodies specific for the lipids in the panel. In some cases, the positive-control IgM antibodies can comprise a detectable label. A subject kit can include an insoluble support having a panel of mycobacterial lipids attached thereto. The panel of lipids comprises cardiolipin, phosphatidylinositol, phosphatidylethanolamine, phosphatidylcholine, and sphingolipid.

In some embodiments, a subject kit includes purified mycobacterial lipids, e.g., where the lipids are provided at greater than 90% purity, greater than 95% purity, greater than 98% purity, or greater than 99% purity. For example, the kit can include one or more of cardiolipin, phosphatidylinositol, phosphatidylethanolamine, phosphatidylcholine, and sphingolipid in purified form. In some instances, a subject kit includes cardiolipin, phosphatidylinositol, phosphatidylethanolamine, phosphatidylcholine, and sphingolipid in purified form. In some instances, a subject kit includes purified mycobacterial lipids immobilized on an insoluble support.

The lipids can be obtained from a variety of sources. For example, the lipids can be obtained from mycobacteria (e.g., purified from mycobacteria); the lipids can be obtained from mammalian host cells (e.g., from mammalian host cells infected with a *mycobacterium*); or the lipids can be obtained from commercial sources. Thus, the term "mycobacterial lipid" refers to a lipid that is associated with a *mycobacterium* and can be synthesized by a *mycobacterium*. However, the term "mycobacterial lipid" does not limit the source of the lipid to mycobacteria.

In some cases, the binding agent that specifically binds human IgM is an antibody. Suitable antibodies include monoclonal antibodies, and antigen-binding fragments (e.g., a Fv, scFv, Fab, F(ab')2, or Fab' fragment). Where the binding reagent is an antibody, the antibody can be immobilized on an insoluble support (e.g., a test strip, a well of a multi-well plate, beads, etc.). Where the binding reagent is an antibody, the antibody can comprise a detectable label. Where the antibody comprises a detectable label, a subject kit can include one or more reagents for developing the detectable label. A labeled antibody can comprise a label such as a chemiluminescent agent, a particulate label (e.g., colloidal gold), a magnetic bead, a colorimetric agent, an energy transfer agent, an enzyme, a fluorescent agent, or a radioisotope. A subject kit can include an anti-IgM antibody coupled to a magnetic bead.

Other optional components of the kit include: a buffer; a protease inhibitor; a lipase inhibitor; a detectable label; etc. The various components of the kit may be present in separate containers or certain compatible components may be pre-combined into a single container, as desired.

A subject kit can include a solid support (also referred to herein as an "insoluble support"). Suitable insoluble supports can comprise various materials including, but not limited to, PVDF, cellulose, nitrocellulose, nylon, glass, polystyrene, polyvinyl chloride, polypropylene, polyester terephthalate, polyethylene, polycarbonate, dextran, amylose, natural and modified celluloses, polyacrylamides, silica embedded in a polyacrylamide gel, agaroses, and magnetite and the like.

In addition to above-mentioned components, a subject kit can include instructions for using the components of the kit to practice a subject method. The instructions for practicing a subject method are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g. compact disc-read only memory (CD-ROM), digital versatile disk (DVD), diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, this means for obtaining the instructions is recorded on a suitable substrate.

Assay Device

The present disclosure further provides an assay device for use in detecting, in a liquid biological sample obtained from an individual, IgM specific for a mycobacterial lipid. The device can include a matrix defining an axial flow path. The matrix can comprise: i) a sample receiving zone at an upstream end of the flow path that receives the liquid sample; ii) one or more test zones positioned within the flow path and downstream from the sample receiving zone, each of the one or more test zones comprising a different mycobacterial lipid immobilized therein, where each of the immobilized mycobacterial lipids is capable of binding mycobacterial lipid-specific IgM present in the liquid sample, to form an immobilized mycobacterial lipid-specific IgM; and iii) one or more control zones positioned within the flow path and downstream from the sample receiving zone, where the one or more control zones can include positive and/or negative controls. The test zones and control zones can be positioned in an alternating format within the flow path beginning with a test zone positioned upstream of any control zone.

Control zones can include, e.g., human IgM (e.g., purified human IgM) in known amounts, e.g., for use in generating a standard curve, such that the amount of mycobacterial lipid-specific human IgM in a liquid biological sample can be quantitated.

In using such an assay device, in some embodiments, a labeled antibody specific for human IgM can first be mixed with a liquid sample before the liquid sample is applied to the sample receiving zone of the device, where such mixing results in a labeled antibody/human IgM complex. In these embodiments, the liquid sample comprising the labeled antibody/human IgM complex is applied to the sample receiving zone of the assay device. The liquid sample flows along the device until the liquid sample reaches a test zone. Lipid present in the test zone binds mycobacterial lipid-specific human IgM present in the labeled antibody/human IgM complex; and can then be detected.

The assay device can further include a label zone comprising a labeled antibody specific for human IgM, wherein the labeled antibody is capable of binding an IgM present in an immobilized IgM-lipid complex to form a labeled immobilized IgM-lipid complex, and wherein the labeled antibody is mobilizable in the presence of liquid sample. In using such an assay device, a liquid sample comprising mycobacterial lipid-specific human IgM is applied to the sample receiving zone of the device; antibody present in the label zone binds the mycobacterial lipid-specific human IgM, forming labeled antibody/mycobacterial lipid-specific human IgM complex, which, like the labeled antibody, is mobilizable; and the labeled antibody/mycobacterial lipid-specific human IgM complex flows along the device until the liquid sample reaches a test zone. Lipid present in the test zone binds mycobacterial lipid-specific human IgM present in the labeled antibody/mycobacterial lipid-specific human IgM complex; and can then be detected.

The labeled antibody can comprise a label such as a chemiluminescent agent, a particulate label (e.g., colloidal gold), a colorimetric agent, an energy transfer agent, an enzyme, a fluorescent agent, or a radioisotope.

Control zones include positive control zones and negative control zones.

The matrix is generally an insoluble support, where suitable insoluble supports include, but are not limited to, polyvinyl difluoride (PVDF), polyester terephthalate, cellulose, nitrocellulose, polystyrene, nylon, silica embedded in polyacrylamide, and the like. The matrix can be flexible, or can be relatively inflexible. The matrix can be positioned within a housing comprising a support and optionally a cover, where the housing contains an application aperture and one or more observation ports. The assay device can be in any of a variety of formats, e.g., a test strip, a dipstick; etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1: Detection of Antibodies to *M. tuberculosis* Lipids in Humans

Materials and Methods
Patient Specimens

Serum samples were obtained at baseline (before initiation of drug therapy) and at the end of the intensive phase of therapy from 40 HIV-negative patients with acid-fast bacilli (AFB) smear and culture-confirmed pulmonary tuberculosis (PTB). These patients were enrolled in a study of the Center for Disease Control and Prevention-Tuberculosis Trials Consortium (CDC-TBTC) randomized clinical trial conducted in Kampala, Uganda. The patient cohort was equally composed of two groups: 20 culture-positive patients (slow responders) and 20 culture-negative patients (fast responders) at the end of 40 doses of anti-TB combination treatment, which corresponds to eight weeks of treatment (5 doses per week). Patients were further categorized according to disease severity, based on the extent of radiological findings in chest X-ray at TB diagnosis including: limited, moderate, and extensive; and whether or not cavitary lesions were present: cavity and no cavity. Serum samples were screened for levels of IgM antibodies against five phospholipids extracted from bovine sources available commercially (Avanti Polar Lipids, Ala., USA).

Enzyme-Linked Immunosorbent Assay (ELISA)

The phospholipid antigens included cardiolipin (CL), phosphatidylinositol (PI), phosphatidylethanolamine (PE), phosphatidylcholine (PTC), and sphingolipid (SL). Lipids were diluted to 10 mg/ml in ethanol and 50 µl of the solutions were dried overnight in flat bottom well polystyrene ELISA plates (Fisher Scientific, USA). ELISA plates were blocked with 100 µl of 3% low fatty acid bovine serum albumin (BSA) (USBiologicals, USA) and washed with phosphate buffered saline (PBS) pH 7.4. Frozen serum samples were thawed twice and diluted 1:100 in 3% low fatty acid BSA. The diluted sample was added to the plate and incubated for one hour at room temperature (RT), followed by three washes with PBS. Then, 100 µl of 1:5,000 goat-derived anti-human IgM labeled with horse radish peroxidase (HRP) (Thermo Scientific, Ill) diluted in PBS pH 7.4 was added, followed by incubation at RT for 1 hr and washed again with PBS. Finally, 100 µl of tetramethylbenzidine substrate (TMB) (Thermo Scientific Pierce, Ill., USA) was added and the reaction was stopped immediately with 50 µl of sulfuric acid 1M.

Reactions were read within ten minutes at 450 nm in a spectrophotometer (Cambridge Technologies, Massachusetts). The results were read out as the average of optical densities (O.D.) of triplicate assays. Standards curves for the ELISA were prepared with polyclonal human IgM (Thermo Scientific Pierce, Ill., USA), which yielded a correlation coefficient $R^2$ of 0.99. The concentration of IgM in serum samples (in µg/ml) was calculated based on this standard curve. High, medium, and low IgM level control samples were included in each assay. Assays with control sample results outside two standard deviations were discarded and repeated.

Statistical Analyses

All statistical analyses were conducted with STATA (Version 11, STATA Corp., Texas). The two-sample Wilcoxon rank-sum test was used to compare lipid-specific IgM concentration differences between fast and slow responders (at baseline and at the end of intensive phase of treatment). A step-wise procedure was performed to test for the following variables suspected to be biologically relevant to IgM antibody response during treatment: age, gender, body mass index (BMI), bilateral abnormalities, acid-fast bacillus (AFB) smear status at baseline, cavitary disease, and disease severity. Variables were added to the basic model in a stepwise fashion. Variables were eliminated if they failed to achieve significance at the 5% level from the full model to obtain the best fit and simplest model that included cavity classification and disease severity as significant variables. The Wilcoxon signed-rank nonparametric test was used to compare lipid-specific antibody differences between groups for cavity and disease severity variables. All experiments were conducted with IRB approval from the Committee for Protection of Human Subjects at UC Berkeley (UCB#2010-06-1752).

Results

The CDC-TBTC sample set was composed of 40 HIV-negative patients (29 males and 11 females) with smear and culture confirmed pulmonary TB. The average age was 29 years (range 19 to 53 years of age). Fifty-five percent of these patients were non-smokers, non-alcoholics, and non drug users (Table 1). Patients with negative culture after 2 months of treatment showed a higher BMI. Three levels of disease severity were identified based on the extent of radiological findings in chest X-ray at TB diagnosis including: limited (n=3), moderate (n=21), and extensive (n=16); and whether or not cavitary lesions were present: cavity (n=23) and no cavity (n=17) (Table 1).

TABLE 1

Demographic and clinical characteristics of TB patients who responded early (sputum culture negative at 8 weeks of treatment) and late (sputum culture positive at 8 weeks).

| | Culture negative at 8 weeks (n = 20) | Culture positive at 8 weeks (n = 20) |
|---|---|---|
| Demographic characteristics | | |
| Age; median (IQR) | 25.0 (6.0) | 30.0 (4.0) |
| Male gender | 13 (65%) | 16 (85%) |
| Social characteristics | | |
| Smoking history | 4 (20%) | 5 (25%) |
| Past alcohol use | 0 (0%) | 1 (5%) |
| Past drug use (injection) | 0 (0%) | 0 (0%) |
| Past drug use (non-injection) | 0 (0%) | 1 (5%) |
| Clinical characteristics | | |
| BMI; median (IQR) | 19.8 (2.8) | 18.6 (2.5) |
| HIV infected | 0 (0%) | 0 (0%) |
| Any co-morbid condition | 1 (5%) | 0 (0%) |
| TB diagnosis | | |
| Any cavity | 12 (60%) | 11 (55%) |
| Bilateral cavitation | 1 (5%) | 2 (10%) |
| Cavity classification | | |
| Absent | 8 (40%) | 9 (45%) |
| Present <4 cm | 5 (25%) | 4 (20%) |
| Present ≥4 cm | 7 (35%) | 7 (35%) |
| Extent of Chest x-ray involvement | | |
| Limited | 0 (0%) | 3 (15%) |
| Moderate | 14 (70%) | 7 (35%) |
| Extensive | 6 (30%) | 10 (50%) |
| Any bilateral abnormalities | 8 (40%) | 12 (60%) |
| AFB smear | | |
| 2+ | 4 (20%) | 0 (0%) |
| 3+ | 6 (30%) | 7 (35%) |
| 4+ | 10 (50%) | 13 (65%) |
| Days to detection; median (IQR) | 5.84 (2.54) | 5.83 (2.38) |
| TB treatment | | |
| Received pretreatment | 4 (20%) | 1 (5%) |
| Days of pretreatment | 0 (0%) | 0 (0%) |

The IgM anti-phospholipid antibody response was highly variable among these patients. A global analysis of our sample set showed heterogeneous results for all five anti-phospholipid IgM levels, regardless of culture conversion status. A comparison of the change in IgM antibody levels between TB patients who remained culture positive and those who culture converted after 40 doses of intense therapy, revealed no significant differences using a two-sample t-test.

The multi-variable model included age, gender, body mass index, bilateral abnormalities, smear status at baseline, cavity extension and disease extension. This model revealed no contribution of the variables to changes in antibody levels upon treatment completion. Thus, we opted to use a simpler model using "cavity classification" as a proxy for disease severity and adjusted for "age". The "cavity classification" variable showed a uniform distribution across three categories, including no cavity (n=17), small cavity (n=9), and large cavity (n=14). This simpler model allowed us to study the IgM anti-phospholipid antibodies as a biomarker for TB treatment response, despite the variability of the antibody levels within our sample set.

Analysis of this simpler model consistently revealed IgM anti-phospholipids antibodies to decrease among TB patients with no lung cavities. Specifically, the mean IgM concentration decreased significantly in four of the five phospholipids, including PE, PI, PTC and SL (paired t-student p=0.008, 0.016, 0.020, and 0.043 respectively). The distribution of delta change among all patients was scattered due to the presence of outliers in the cavity classification categories. The median values of antibody change were analyzed with a two-sample Wilcoxon rank-sum test. This revealed a significant decrease for all five lipids, CL, PI, PE, PTC, and SL in non-cavitary TB patients (Wilcoxon rank-sum test p=0.036, 0.006, 0.001, 0.007, 0.040 respectively, see FIG. 1). The antibody level reduction was different for each lipid. Specifically, we observed a 22.7%, 11.1%, 15.4%, 24.3% and 18.0% concentration reduction of IgM anti-CL, PE, PI, PTC and SL, respectively.

On the other hand, patients with cavitary TB showed an overall increase in the IgM anti-phospholipid antibody response following anti-TB drug treatment. A significant increase was observed in anti-PE antibody levels (p=0.025, 95% C.I. −0.091, −0.004).

FIG. 1: Plots of the Change of IgM Anti-Phospholipids Antibody Levels after 40 Doses of Intense Anti-TB Drug Therapy.

Antibody levels were determined by in-house ELISA assay; and results are shown in concentration (μg/ml). The panels compare the antibody decrease in Cavitary TB patients vs Non-cavitary TB patients for each of the five phospholipids including Cardiolipin (CL); phosphatidyl ethanolamine (PE); Phosphatidyl Inositol (PI); Phosphatidyl Choline (PTC); Sphingolipid (SL).

We evaluated our biomarker test's ability to identify successful treatment response in non-cavitary TB patients. A positive biomarker test was defined as a decrease in IgM anti-phospholipid antibodies and a negative test as an increase or no change in IgM anti-phospholipid antibodies. The outcome was successful treatment response. The sensitivity values for the phospholipid-antibody biomarker test were 88.2%, 70.6%, 76.5%, 88.2% and 76.5% for IgM anti-CL, PE, PI, PTC and SL, respectively (Table 2). Taken together, the mean sensitivity reached 80%.

TABLE 2

Biomarker test evaluation for monitoring treatment response in non-cavitary TB[a].

|  | Non-Cavitary TB decreased | Sensitivity % |
| --- | --- | --- |
| CL | 15/17 | 88.2 |
| PE | 12/17 | 70.6 |
| PI | 13/17 | 76.5 |
| PtC | 15/17 | 88.2 |
| SL | 13/17 | 76.5 |

[a]Number of non-cavitary TB patients that showed a decrease in IgM anti-phospholipid antibody levels. Values for sensitivity were determined for each lipid using contingency table analysis.

Figure 2:
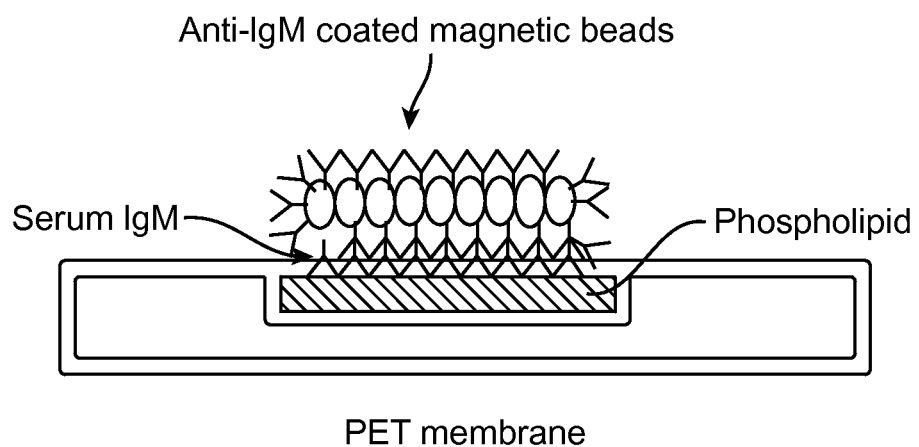
FIG. 2 is a schematic representation of a magnetic bead-linked immunosorbent assay (mLISA).
Figure 3:
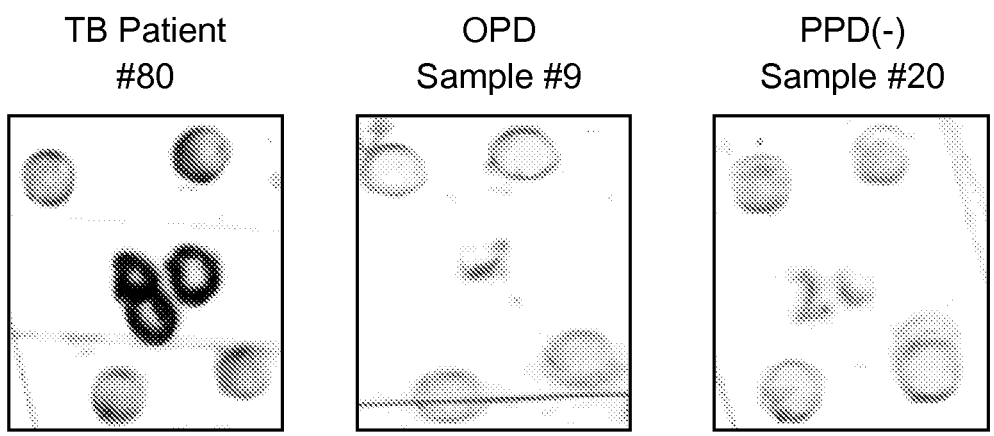
FIG. 3 depicts sample results of membranes from an mLISA (OPD-patients with pulmonary disease other than TB, PPD-patients testing positive for tuberculin skin test).

Example 2: Detection of IgM Antibody to M. tuberculosis Lipids Using a Magnetic Bead-Linked Immunosorbent Assay A magnetic bead-linked immunosorbent assay (mLISA) was developed to detect IgM antibody to M. tuberculosis lipids. The mLISA assay is depicted schematically in FIG. 2. Streptavidin-coated magnetic beads linked to biotin-conjugated anti-IgM antibody were used. A small drop (2 microliters) of phospholipid solution in ethanol was spotted onto wells made by a 2.5 mm biopsy punch on a 2×2 cm piece of polyester terephthalate (PET) membrane (Rogers Corp., IL, USA). The ethanol was allowed to dry for thirty minutes, and the membrane was washed with phosphate-buffered saline (PBS) (1M, pH 7.2). The membrane was then blocked with 5 μl of 2% bovine serum albumin (BSA) (low fatty acid, low endotoxin, low IgG) (US Biological, Swampscott, Mass., USA) for one hour. The membrane was washed again with PBS; and 5 μl of undiluted patient serum was applied to each well and incubated for two hours in a wet chamber to prevent evaporation. The membrane was washed again, and a 5 μl suspension of the anti-IgM-coated magnetic bead was added to each well and incubated for twenty minutes, followed by another PBS wash. The membrane was then visualized with the unaided eye for rusty-colored spots in the wells, which indicated a positive test reaction. A visual representation of the assay is shown in FIG. 3.

The intensity of the color at each spot was quantitatively compared by software ImageJ. Table 3 summarizes results based on serum samples obtained from 29 culture-confirmed cases of TB (TB patients), 16 patients with pulmonary disease other than TB (OPD), and 19 healthy subjects whose tuberculin skin test was negative, indicating no evidence of TB infection (TST-).

Table 3. Results of mLISA based on serum samples tested against cardiolipin (CL), phosphotidylethanolamine (PE), phophatidylinositol (PI), phosphotidylcholine (PTC), and sphingolipid (SL) embedded in PET wells. The well images were converted into 16-bit black and white photos, and particle density was measured in each well. The readings from 4 spots on one piece of membrane (2×2 cm) were combined to calculate an average reading per membrane. Student T test was used to compare the results.

TABLE 3

| Comparison Groups | CL | PE | PI | PTC | SL |
| --- | --- | --- | --- | --- | --- |
| TB patient v. TST− | <0.001 | <0.001 | <0.001 | <0.001 | <0.001 |
| TB patient v. OPD | <0.001 | 0.009 | 0.014 | 0.031 | 0.072 |
| TST− v. OPD | 0.049 | 0.014 | 0.003 | 0.004 | 0.002 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of determining response in a human individual to treatment for a non-cavitary Mycobacterium tuberculosis infection, the method comprising determining the level of IgM specific for two or more different M. tuberculosis lipids in a biological sample obtained from the individual, wherein a level of M. tuberculosis lipid-specific IgM in the biological sample that is lower than a pre-treatment level in a control sample of the same type as the biological sample indicates that the individual is responding positively to the treatment.

2. The method of claim 1, wherein the two or more M. tuberculosis lipids are selected from cardiolipin, phosphatidylinositol, phosphatidylethanolamine, phosphatidylcholine, and sphingolipid.

3. The method of claim 1, wherein the biological sample is blood, a blood fraction, cerebrospinal fluid, pleural fluid, bronchoalveolar lavage fluid, or saliva.

4. The method of claim 1, wherein the two or more different *M. tuberculosis* lipids are selected from phosphatidylinositol, phosphatidylethanolamine, phosphatidylcholine, and sphingolipid.

5. An assay device for use in detecting IgM specific for a *Mycobacterium tuberculosis* lipid in a liquid biological sample obtained from an individual, the device comprising a matrix defining an axial flow path, the matrix comprising:
   i) a zone one comprising a sample receiving zone at an upstream end of the flow path configured to receive the fluid sample;
   ii) a zone three comprising one or more test zones positioned within the flow path and downstream from zone one, each of said one or more test zones comprising a *Mycobacterium tuberculosis* lipid immobilized in each of said test zones, wherein each of said immobilized lipids is capable of binding a *M. tuberculosis* lipid-specific IgM present in said liquid sample to form an immobilized IgM-lipid complex;
   iii) a zone two comprising a label zone comprising a detectably labeled antibody specific for human IgM, wherein the label zone is positioned within the flow path configured to receive the sample from zone one and is downstream of zone one and upstream of zone three, wherein the detectably labeled antibody is capable of binding an IgM present in an immobilized IgM-lipid complex to form a labeled immobilized IgM-lipid complex, and wherein the detectably labeled antibody is capable of binding to the human IgM present in the liquid sample to form a labeled antibody/human IgM complex that is configured to flow to the one or more test zones of zone three; and
   iv) a zone four comprising one or more control zones positioned within the flow path and downstream from zone one, each of said one or more control zones comprising a positive control comprising immobilized human IgM in a known amount, or a negative control comprising no *M. tuberculosis* lipids, wherein zone four is configured to receive the sample from zone one, wherein the *M. tuberculosis* lipid-specific IgM is detected when the detectably labeled antibody specific for human IgM is bound to the immobilized IgM-lipid complex.

6. A kit for determining the level of IgM specific for two or more different *Mycobacterium tuberculosis* lipids in a biological sample obtained from an individual, the kit comprising:
   a) an anti-IgM antibody comprising a detectable label; and
   b) a panel of two or more different *Mycobacterium tuberculosis* lipids.

7. The kit of claim 6, further comprising purified human IgM for use in generating a standard curve.

8. The kit of claim 6, further comprising a panel of positive control IgM antibodies specific for the lipids in the panel.

9. The kit of claim 6, further comprising an insoluble support having the panel of lipids attached thereto.

10. The kit of claim 6, wherein the panel of lipids comprises cardiolipin, phosphatidylinositol, phosphatidylethanolamine, phosphatidylcholine, and sphingolipid.

11. A method for detecting the presence of *Mycobacterium tuberculosis* in an individual, the method comprising detecting IgM specific for two or more different *Mycobacterium tuberculosis* lipids in a liquid biological sample obtained from the individual, wherein the presence in the biological sample of IgM specific for two or more different *Mycobacterium tuberculosis* lipids indicates the presence in the individual of *Mycobacterium tuberculosis*, and wherein the step of detecting the IgM comprises:
   a) contacting two or more different, immobilized *Mycobacterium tuberculosis* lipids with the liquid biological sample, wherein any IgM specific for the immobilized *Mycobacterium tuberculosis* lipids binds the immobilized *Mycobacterium tuberculosis* lipids, forming an immobilized *Mycobacterium tuberculosis* lipid-IgM complex; and
   b) contacting the immobilized *Mycobacterium tuberculosis* lipid-IgM complex with detectably labeled anti-IgM antibody, wherein the anti-IgM antibody forms a complex with the immobilized *Mycobacterium tuberculosis* lipid-IgM; and
   c) detecting the anti-IgM antibody present in the anti-IgM-immobilized *Mycobacterium tuberculosis* lipid-IgM complex.

12. The method of claim 11, wherein the two or more different, immobilized *M. tuberculosis* lipids are selected from cardiolipin, phosphatidylinositol, phosphatidylethanolamine, phosphatidylcholine, and sphingolipid.

13. The method of claim 11, wherein the biological sample is blood, a blood fraction, cerebrospinal fluid, pleural fluid, bronchoalveolar lavage fluid, or saliva.

14. The method of claim 11, wherein the anti-IgM antibody is coupled to a magnetic bead, an enzyme that generates a fluorescent product, an enzyme that generates a colored product, a fluorescent polypeptide, or a chromogenic polypeptide.

15. The method of claim 14, wherein the anti-IgM antibody is coupled to a magnetic bead.

16. The method of claim 15, wherein coupling of the anti-IgM antibody to the magnetic bead comprises binding of an anti-IgM antibody covalently linked to a biotin to the magnetic bead coated with a streptavidin to form a stable anti-IgM magnetic bead complex.

17. The method of claim 15, wherein coupling of the anti-IgM antibody to the magnetic bead comprises binding of an anti-IgM antibody to the magnetic bead, wherein the magnetic bead is cross-linked to a protein G or a protein A.

18. The method of claim 11, wherein said individual is co-infected with human immunodeficiency virus.

19. The method of claim 11, wherein said individual has non-cavitary lung disease.

20. The method of claim 11, wherein the labeled antibody is mobilizable in the presence of the liquid sample.

21. The method of claim 11, wherein the labeled anti-IgM antibody comprises a label selected from the group consisting of:
   a) a chemiluminescent agent;
   b) a particulate label;
   c) a colorimetric agent;
   d) an energy transfer agent;
   e) an enzyme;
   f) a fluorescent agent; and
   g) a radioisotope.

22. The method of claim 21, wherein the particulate label is a colloidal gold.

* * * * *